United States Patent
Lou et al.

(10) Patent No.: US 6,294,539 B1
(45) Date of Patent: Sep. 25, 2001

(54) HETEROCYCLIC HYDROXAMIC ACID DERIVATIVES AS MMP INHIBITORS

(75) Inventors: Boliang Lou, Louisville, KY (US); Adnan M. M. Mjalli, Jamestown, NC (US)

(73) Assignee: Advanced Syntech, LLC, Louisville, KY (US)

( * ) Notice: Subject to any disclaimer, the term of this patent is extended or adjusted under 35 U.S.C. 154(b) by 0 days.

(21) Appl. No.: 09/487,528

(22) Filed: Jan. 19, 2000

Related U.S. Application Data

(60) Provisional application No. 60/116,250, filed on Jan. 19, 1999.

(51) Int. Cl.[7] ........................ A61K 31/495; C07D 241/04
(52) U.S. Cl. ............................... 514/255.01; 514/255.02; 514/255.03; 514/255.05; 544/358; 544/386
(58) Field of Search ................... 514/255.01, 255.02, 514/255.03, 255.05; 544/358, 386

(56) References Cited

FOREIGN PATENT DOCUMENTS

WO 96/40737 * 12/1996 (WO).

* cited by examiner

*Primary Examiner*—Mukund J. Shah
*Assistant Examiner*—Sudhaker B. Patel
(74) *Attorney, Agent, or Firm*—John E. Vanderburgh

(57) ABSTRACT

Novel compositions comprising heterocyclic hydroxamic acid derivatives of the general formula:

Formula (1)

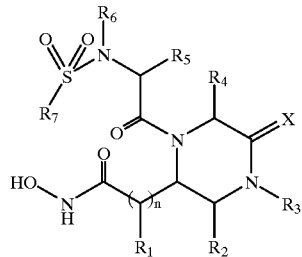

These compounds are useful in the treatment of diseases and conditions in which matrix metalloproteinases are involved, such as cancer, arthritis, tumor metastasis and multiple sclerosis (MS).

10 Claims, No Drawings

HETEROCYCLIC HYDROXAMIC ACID DERIVATIVES AS MMP INHIBITORS

CROSS REFERENCE TO RELATED APPLICATIONS

This application claims the benefit of provisional application Ser. No. 60/116,250, filed Jan. 19, 1999 in the name of Boliang Lou and Adnan M. M. Mjalli.

FIELD OF THE INVENTION

The present invention relates to heterocyclic hydroxamic acid derivatives which inhibit matrix metalloproteinases and such are useful in the treatment of diseases and conditions in which matrix metalloproteinases are involved, such as cancer, arthritis, tumor metastasis and multiple sclerosis (MS).

BACKGROUND OF THE INVENTION

The matrix metalloproteinases (MMP) are a family of zinc containing enzymes that degrade extracellular matrices. They are excreted by a variety of connective tissue and pro-inflammatory cells including fibroblasts, osteoblasts, endothelial cells, macrophages, neutrophils, and lymphocytes. Most are excreted as inactive proenzymes and then activated extracellularly by serine proteases or other MMPs. Over the last decade the MMP family has grown rapidly. At least 16 members have now been identified, which are divided into four families by virtue of similarities of their domain structures (W. C. Powell, et al, *Curr. Top. Microbiol. Immunol.* 213, 1, 1996). They include the Minimal Domain family with the only member (MMP-7), the Hemopexin Domain family (e.g. MMP-1, MMP-3, MMP-8, MMP-10, MMP-11, MMP-12, and MMP-13), the Fibronectin Domain family (e.g. MMP-2 and MMP-9) and the most recently discovered Transmembrane Domain family (e.g. MMP-14- MMP-17).

The MMPs have been extensively reviewed including a book ("Matrix Metallo-proteinases", edited by William C. Parks and Robert P. Mecham, 1998, Academic Press). A role for these enzymes has been implicated in both normal and pathological processes. The loss of control of MMP activity and the elevated levels in MMP expression have been associated with several diseases. The proposed pathogenic roles for MMPs include the destruction of cartilage and bone in rheumatoid arthritis and osteoarthritis (T. E. Cawston, *Pharm. Ther.* 70, 163, 1996; E. M. O'Byrne, et al; *Inflam. Res.* 44, S117, 1995), tissue breakdown and remodeling during invasive tumor growth and tumor angiogenesis (L. A. Liotta, et al, *Sem. Camer Biol.* 1, 99, 1990), degradation of myelin-basic protein in neuroinflammatory diseases (K. Gijbels, et al, *J. Neuroimmunol.* 41, 29, 1992; S. Chandler, et al, *Neurosci. Lett.* 201, 223, 1995), opening of the blood-brain barrier following brain injury (G. A. Rosenberg, *J. Neurotrauma,* 12, 833,1995), increased matrix turnover in restenotic lesions (B. H. Strauss, et al, *Circ. Res.* 79, 541, 1996), loss of aortic wall strength in aneuryms (R. W. Thompson, et al, *Ann. N.Y. Acad. Sci.* 800, 157, 1996), and tissue degradation in gastric ulceration (U. K. Saarialho-Kere, et al, *Am. J. Pathol.* 148, 519, 1996).

In view of the involvement of MMPs in a variety of disease states, the inhibition of these enzymes as a therapeutic target is now an area of intense interest within the pharmaceutical industry. A large number of such inhibitors have been identified and disclosed in the literature. Examples include WO9633166, WO9718207, and WO9633176 (Dupont Merck Pharm. Co.); U.S. Pat. No. 5,691,382, WO9625156, WO9702239, WO9719053, WO9718183, WO9719050, WO9633161, GB-2298423-A, WO9633165, WO9535275, WO9535276, WO9626233, and WO9703783 (British Biotech Pharm. Ltd.); WO9506031 and WO9641624 (Immunex Corp.); WO9709420 and WO9709430 (Celltech Therapeutics Ltd.); WO9742168 (Zeneca Ltd.); WO9749674, WO9732846, WO9740031, and WO9748688 (Pharmacia & Upjohn); WO9602240, WO9725981, WO9726257, WO9743250, WO9743249, and WO9523790 (SmithKline Beecham); WO9633991, WO9715553, and WO9731892 (Sankyo Co. Ltd.); WO9747599 (Fujisawa Pharm. Co. Ltd.); WO9633968 (Fuji Yakuhin Kogyo KK); WO9421612, JP8081443-A, and JP8325232-A (Otsuka Seiyaku KK); EP-0606046 (Ciba-Geigy AG); WO9722587 (Novartis AG); WO9720824 (Agouron Pharm., Inc.); WO9633172 (Pfizer, Inc.); WO9718194 (Hoechst AG); EP-0757984, WO9745402, EP-0757037, and WO9749679 (Ono Pharma Co. Ltd.); WO9727174 (Shionogi & Co. Ltd.); WO9719068, WO9744315, WO9723459, and WO9638434 (Warmer-Lambert Co.); EP-0780386-A1 (Hoffmann-La Roche AG & Agouron Pharm., Inc.); WO9724117 (Rhone-Poulenc Rorer Pharm., Inc.); WO9718469 and WO9718188 (Abbott Lab.); WO9615096, WO9743237, WO9743245, WO9743238, WO9743240, WO9743247, and WO9743239 (Bayer Corp.); WO9221360, WO9412169, and WO9711936 (Merck & Co., Inc.); WO9635711, WO9635712, WO9635714, WO9635687, WO9712861, WO9712902, WO9719075, WO9737973, WO9737974, and WO9738007 (Chiroscience Ltd.); WO9640204 (Affymax Tech. NV); WO9748685 (Glaxo Group Ltd.); WO9640745 (Osteoarthritis Sciences, Inc.); EP-0758021 (Polifarma SPA); EP-0758649 (Kureha Chem. Ind. Co. Ltd.). However, the majority of these inhibitors are peptidyl or peptide-like compounds which may exhibit a lack of bioavailability and poor pharmacokinetic profile. There is a continuing need for small molecule-based highly potent and orally bioavailable inhibitors useful in treating such diseases.

SUMMARY OF THE INVENTION

The present invention relates to heterocyclic hydroxamic acid derivatives of the general formula:

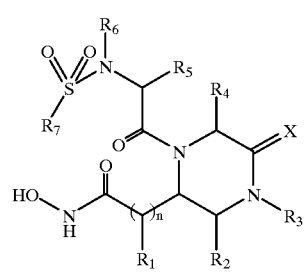

Formula (1)

These compounds are useful in the treatment of diseases and conditions in which matrix metalloproteinases are involved, such as cancer, arthritis, tumor metastasis and multiple sclerosis (MS).

DESCRIPTION OF THE INVENTION

The present invention provides novel compounds of Formula (I) or pharmaceutical

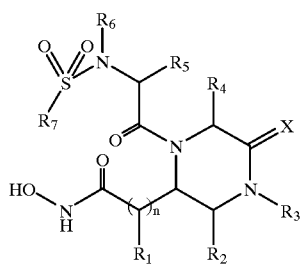

Formula (1)

acceptable salts thereof; wherein the broken line represents an optional double bond;

X is H, O, S;

n is 0 or 1;

$R_1$ is hydrogen, hydroxy, thio, nitro, cyano, azido, amino, trifluoromethyl, trifluoromethoxy, $C_1$–$C_6$ alkyl, $C_1$–$C_6$ alkyloxy, $C_1$–$C_6$ alkylthio, $C_1$–$C_6$ alkylamino, $C_1$–$C_6$ alkenyl, $C_1$–$C_6$ alkenyloxy, $C_1$–$C_6$ alkenylamino, $C_3$–$C_8$ cycloalkyl, $C_3$–$C_8$ cycloalkyloxy, $C_3$–$C_8$ cycloalkylamino, $C_3$–$C_8$ cycloalkylthio, $C_1$–$C_6$ alkylcarbonylamino, $C_3$–$C_8$ cycloalkylcarbonylamino, $C_5$–$C_{10}$ aryl, $C_5$–$C_{10}$ heteroaryl or $C_5$–$C_{10}$ saturated heteroaryl; said aryl, heteroaryl, alkyl, alkenyl, and cycloalkyl optionally substituted with 1 to 3 groups of $R_s$;

$R_2$, $R_3$, $R_4$, $R_5$, and $R_6$ independently are H, trifluoromethyl, $C_5$–$C_{10}$ aryl, $C_5$–$C_{10}$ heteroaryl, $C_1$–$C_{10}$ alkyl, $C_2$–$C_{10}$ alkenyl, $C_2$–$C_{10}$ alkynyl, $C_3$–$C_{10}$ cycloalkyl, saturated $C_5$–$C_{10}$ heteroaryl, $C_5$–$C_{10}$ aryl-$C_1$–$C_{10}$ alkyl, $C_5$–$C_{10}$ heteroaryl-$C_1$–$C_{10}$ alkyl, $COR_8$, $CO_2R_8$, $CONR_8R_9$, $SO_2NR_8R_9$, said aryl, heteroaryl, alkyl, alkenyl, and cycloalkyl optionally substituted with 1 to 3 groups of $R_s$;

$R_7$ is $C_5$–$C_{10}$ aryl, $C_5$–$C_{10}$ heteroaryl, $C_1$–$C_6$ alkyl, $C_2$–$C_6$ alkenyl, $C_3$–$C_6$ cycloalkyl, saturated $C_5$–$C_{10}$ heteroaryl, said aryl, heteroaryl, alkyl, alkenyl, and cycloalkyl optionally substituted with 1 to 3 groups of $R_s$;

$R_8$ and $R_9$ independently are H, hydroxy, $C_1$–$C_{10}$ alkyl, $C_2$–$C_{10}$ alkenyl, $C_2$–$C_{10}$ alkynyl, $C_3$–$C_{10}$ cycloalkyl, $C_5$–$C_{10}$ aryl, $C_5$–$C_{10}$ heteroaryl, said aryl, heteroaryl, alkyl, alkenyl, and cycloalkyl optionally substituted with 1 to 3 groups of $R_s$;

$R_s$ represents a member selected from the group consisting of halo, cyano, nitro, trihalomethyl, carbamoyl, hydroxy, $OCF_3$, acyl, aryl, heteroaryl, $S(O)R_8$, $=N(OR_8)$, $SO_2R_8$, $COOR_8$, $-CONR_8R_9$, $-C_1$–$C_6$alkyl$CONR_8R_9$, $C_1$–$C_6$alkyloxy, aryloxy, aryl$C_1$–$C_6$alkyloxy, thio, $C_1$–$C_6$alkylthio, arylthio, aryl$C_1$–$C_6$alkylthio, $NR_7R_8$, $C_1$–$C_6$alkylamino, arylamino, aryl$C_1$–$C_6$alkylamino, di(aryl$C_1$–$C_6$alkyl)amino, $C_1$–$C_6$alkylcarbonyl, aryl$C_1$–$C_6$alkylcarbonyl, $C_1$–$C_6$alkylcarboxy, aryl$C_1$–$C_6$alkylcarboxy, $-NR_7CO_2R_8$, $-NR_7COR_8$, $-NR_9O_2R_8$, $-NR_9O_2R_8$, $-CONR_8R_9$, $-SO_2NR_8R_9$, $-OCONR_8R_9$, $-C_1$–$C_6$alkylamino$CONR_8R_9$, aryl$C_1$–$C_6$alkylcarbonylamino, tetrahydrofuryl, morpholinyl, piperazinyl, or a saturated or partial saturated cyclic 5,6 or 7 membered amine or lactam; said aryl, and heteroaryl optionally substituted with 1 to 3 groups of halo or $C_1$–$C_6$alkyl; wherein $R_8$ and $R_9$ are defined as above.

Definitions

As used herein, the "-" (e.g. $-COR_8$ which indicates the carbonyl attachment point to the scaffold) signifies a stable covalent bond, certain preferred points of attachment points being apparent to those skilled in the art.

The term "halogen" or "halo" include fluorine, chlorine, bromine, and iodine.

The term "alkyl" includes $C_1$–$C_{12}$ saturated aliphatic hydrocarbon groups unless otherwise defined. It may be straight or branched alkyl groups. Branched means that one or more lower alkyl groups such as methyl, ethyl, or propyl are attached. The alkyl group may be substituted by one or more hydroxy, halo, cycloalkyl, cycloalkenyl or heterocyclyl. Examplary alkyl groups include methyl, ethyl, fluoromethyl, difluoromethyl, trifluoromethyl, cyclopropylmethyl, cyclopentylmethyl, n-propyl, i-propyl, n-butyl, t-butyl, n-pentyl, 3-pentyl, heptyl, octyl, nonyl, decyl, and the like. When substituted alkyl is present, this refers to a straight, branched or cyclic alkyl group as defined above, substituted with 1–3 groups as defined with respect to each variable.

The term "alkenyl" includes $C_2$–$C_{12}$ aliphatic hydrocarbon groups containing at least one carbon to carbon double bond and which may be straight or branched unless otherwise defined. Preferably one carbon to carbon double bond is present, up to four non-aromatic carbon to carbon double bond may present. Branched means one or more lower alkyl groups such as methyl, ethyl or propyl are attached to a linear alkenyl chain. "Lower alkenyl" means about 2 to about 4 carbon atoms in the chain which may be straight or branched. For example, this definition shall include but is not limited to ethenyl, propenyl, butenyl, and cyclohexylbutenyl, decenyl, and the like. As described above with respect to alkyl, the straight, branched and cyclic portion of the alkenyl group may contain double bonds and may be substituted when substituted alkenyl group is provided.

The term "alkynyl" includes $C_2$–$C_{12}$ aliphatic hydrocarbon groups containing at least one carbon to carbon triple bond and which may be straight or branched unless otherwise defined. Preferably one carbon to carbon double bond is present, up to carbon to carbon triple bond may present. Branched means one or more lower alkyl groups such as methyl, ethyl or propyl are attached to a linear alkynyl chain. "Lower alkynyl" means about 2 to about 4 carbon atoms in the chain which may be straight or branched. For example, this definition shall include but is not limited to ethynyl, propynyl, butynyl, and the like. As described above with respect to alkyl, the straight, branched and cyclic portion of the alkynyl group may contain triple bonds and may be substituted when substituted alkynyl group is provided.

The term "cycloalkyl" means a non-aromatic mono- or multicyclic ring system of about 3 to about 10 atoms. Preferred monocyclic cycloalkyl rings include cyclopentyl, fluorocyclopentyl, cyclohexyl and halocyclohexyl and cycloheptyl; More preferred is cyclohexyl. The cycloalkyl group may be substituted by one or more halo, methylene ($CH_2=$), alkyl, fused aryl and fused heteroaryl.

The term "cycloalkenyl" means a non-aromatic mono- or multicyclic ring system containing a carbon-carbon double bond and having about 3 to about 10 atoms. Preferred monocyclic cycloalkyl rings include cyclopentenyl, cyclohexenyl and halocyclohexenyl and cycloheptenyl; More preferred is cyclohexenyl. The cycloalkyl group may be substituted by one or more halo, methylene ($CH_2=$), alkyl, fused aryl and fused heteroaryl.

The term "heterocyclyl" means an about 4 to about 10 member monocyclic or multicyclic ring system wherein one or more of the atoms in the ring system is an element other than carbon chosen amongst nitrogen, oxygen or sulfur. The heterocyclyl may be optionally substituted by one or more alkyl group substituents. Examplary heterocyclyl moieties include quinuclidine, pentamethylenesulfide, tetrahedropyranyl, tetrahydrothiophenyl, pyrrolidinyl or tetrahydrofuranyl.

The term "alkyloxy" (e.g. methoxy, ethoxy, propyloxy, allyloxy, cyclohexyloxy) represents an "alkyl" group as defined above having the indicated number of carbon atoms attached through an oxygen bridge. The term "alkyloxyalkyl" represents an "alkyloxy" group attached through an alkyl group as defined above having the indicated number of carbon atoms.

The term "aryloxy" (e.g. phenoxy, naphthyloxy and the like) represents an aryl group as defined below attached through an oxygen bridge.

The term "arylalkyloxy" (e.g. phenethyloxy, naphthylmethyloxy and the like) represents an "arylalkyl" group as defined below attached through an oxygen bridge.

The term "arylalkyloxyalkyl" represents an "arylalkyloxy" group as defined above attached through an "alkyl" group defined above having the indicated number of carbon atoms.

The term "arylthio" (e.g. phenylthio, naphthylthio and the like) represents an "aryl" group as defined below attached through a sulfur bridge.

The term "alkyloxycarbonyl" (e.g. methylformate, ethylformat and the like) represents and "alkyloxy" group as defined above attached through a carbonyl group.

The term "aryloxycarbonyl" (e.g. phenylformate, 2-thiazolylformiat and the like) represents an "aryloxy" group as defined above attached through a carbonyl group.

The term "arylalkyloxycarbonyl" (e.g. benzylformate, phenylethylformiat and the like) represents an "arylalkyloxy" group as defined above attached through a carbonyl group.

The term "alkyloxycarbonylalkyl" represents an "alkyloxycarbonyl" group as defined above attached through an "alkyl" group as defined above having the indicated number of carbon atoms.

The term "arylalkyloxycarbonylalkyl" represents an "arylalkyloxycarbonyl" group as defined above attached through an "alkyl" group as defined above having the indicated number of carbon atoms.

The term "alkylthio" (e.g. methylthio, ethylthio, propylthio, cyclohexylthio and the like) represents an "alkyl" group as defined above having the indicated number of carbon atoms attached through a sulfur bridge.

The term "arylalkylthio" (e.g. phenylmethylthio, phenylethylthio, and the like) represents an "arylalkyl" group as defined above having the indicated number of carbon atoms attached through a sulfur bridge.

The term "alkylthioalkyl" represents an "alkylthio" group attached through an alkyl group as defined above having the indicated number of carbon atoms.

The term "arylalkylthioalkyl" represents an "arylalkylthio" group attached through an alkyl group as defined above having the indicated number of carbon atoms.

The term "alkylamino" (e.g. methylamino, diethylamino, butylamino, N-propyl-N-hexylamino, (2-cyclopentyl) propylamino, pyrrolidinyl, piperidinyl, and the like) represents one or two "alkyl" groups as defined above having the indicated number of carbon atoms attached through an amine bridge. The two alkyl groups may be taken together with the nitrogen to which they are attached forming a cyclic or bicyclic system containing 3 to 11 carbon atoms and 0 to 2 additional heteroatoms selected from nitrogen, oxygen or sulfur, the ring system can optionally be substituted with at least one $C_1$–$C_6$alkyl, aryl, aryl$C_1$–$C_6$alkyl, hydroxy, $C_1$–$C_6$alkyloxy, $C_1$–$C_6$alkyloxy$C_1$–$C_6$alkyl, $NRR_8$, $C_1$–$C_6$alkylamino$C_1$–$C_6$alkyl substituent wherein the alkyl and aryl groups are optionally substituted as defined in the definition section and R and $R_8$ are defined as above.

The term "arylalkylamino" (e.g. benzylamino, diphenylethylamino and the like) represents one or two "arylalkyl" groups as defined above having the indicated number of carbon atoms attached through an amine bridge. The two "arylalkyl" groups may be taken together with the nitrogen to which they are attached forming a cyclic or bicyclic system containing 3 to 11 carbon atoms and 0 to 2 additional heteroatoms selected from nitrogen, oxygen or sulfur, the ring system can optionally be substituted with at least one $C_1$–$C_6$alkyl, aryl, aryl$C_1$–$C_6$alkyl, hydroxy, $C_1$–$C_6$alkyloxy, $C_1$–$C_6$alkyloxy$C_1$–$C_6$alkyl, $NRR_8$, $C_1$–$C_6$alkylamino$C_1$–$C_6$alkyl substituent wherein the alkyl and aryl groups are optionally substituted as defined in the definition section and $R_7$ and $R_8$ are defined as above.

The term "alkylaminoalkyl" represents an "alkylamino" group attached through an alkyl group as defined above having the indicated number of carbon atoms.

The term "arylalkylaminoalkyl" represents an "arylalkylamino" group attached through an alkyl group as defined above having the indicated number of carbon atoms.

The term "arylalkyl" (e.g. benzyl, phenylethyl) represents an "aryl" group as defined below attached through an alkyl having the indicated number of carbon atoms or substituted alkyl group as defined above.

The term "alkylcarbonyl" (e.g. cyclooctylcarbonyl, pentylcarbonyl) represents an "alkyl" group as defined above having the indicated number of carbon atoms attached through a carbonyl group.

The term "arylalkylcarbonyl" (e.g. phenylcyclopropylcarbonyl, phenylethylcarbonyl and the like) represents an "arylalkyl" group as defined above having the indicated number of carbon atoms attached through a carbonyl group.

The term "alkylcarbonylalkyl" represents an "alkylcarbonyl" group attached through an "alkyl" group as defined above having the indicated number of carbon atoms.

The term "arylalkylcarbonylalkyl" represents an "arylalkylcarbonyl" group attached through an alkyl group as defined above having the indicated number of carbon atoms.

The term "alkylcarboxy" (e.g. heptylcarboxy, cyclopropylcarboxy, 3-pentenylcarboxy) represents an "alkylcarbonyl" group as defined above wherein the carbonyl is in turn attached through an oxygen bridge.

The term "arylalkylcarboxy" (e.g. benzylcarboxy, phenylcyclopropylcarboxy and the like) represents an "arylalkylcarbonyl" group as defined above wherein the carbonyl is in turn attached through an oxygen bridge.

The term "alkylcarboxyalkyl" represents an "alkylcarboxy" group attached through an "alkyl" group as defined above having the indicated number of carbon atoms.

The term "arylalkylcarboxyalkyl" represents an "arylalkylcarboxy" group attached through an "alkyl" group as defined above having the indicated number of carbon atoms.

The term "alkylcarbonylamino" (e.g. hexylcarbonylamino, cyclopentylcarbonylaminomethyl, methylcarbonylaminophenyl) represents an "alkylcarbonyl" group as defined above wherein the carbonyl is in turn attached through the nitrogen atom of an amino group. The nitrogen atom may itself be substituted with an alkyl or aryl group.

The term "arylalkylcarbonylamino" (e.g. benzylcarbonylamino and the like) represents an "arylalkylcarbonyl" group as defined above wherein the carbonyl is in turn attached through the nitrogen atom of an amino group. The nitrogen atom may itself be substituted with an alkyl or aryl group.

The term "alkylcarbonylaminoalkyl" represents an "alkylcarbonylamino" group attached through an "alkyl" group as defined above having the indicated number of carbon atoms. The nitrogen atom may itself be substituted with an alkyl or aryl group.

The term "arylalkylcarbonylaminoalkyl" represents an "arylalkylcarbonylamino" group attached through an "alkyl" group as defined above having the indicated number of carbon atoms. The nitrogen atom may itself be substituted with an alkyl or aryl group.

The term "alkylcarbonylaminoalkylcarbonyl" represents an "alkylcarbonylaminoalkyl" group attached through a carbonyl group. The nitrogen atom may be further substituted with an "alkyl" or "aryl" group.

The term "aryl" represents an unsubstituted, mono-, di- or trisubstituted monocyclic, polycyclic, biaryl aromatic groups covalently attached at any ring position capable of forming a stable covalent bond, certain preferred points of attachment being apparent to those skilled in the art. Aryl thus contains at least one ring having at least 5 atoms, with up to two such rings being present, containing up to 10 atoms therein, with alternating (resonating) double bonds between adjacent carbon atoms. Aryl groups may likewise be substituted with 0–3 groups selected from $R_s$. The definition of aryl includes but is not limited to phenyl, biphenyl, indenyl, fluorenyl, naphthyl (1-naphtyl, 2-naphthyl).

Heteroaryl is a group containing from 5 to 10 atoms, 1–4 of which are heteroatoms, 0–4 of which heteroatoms are nitrogen, and 0–1 of which are oxygen or sulfur, said heteroaryl groups being substituted with 0–3 groups selected from $R_s$. The definition of heteroaryl includes but is not limited to pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl, 1,2,3-triazol-4-yl, 1,2,4-triazol-3-yl), oxazolyl (2-oxazolyl, 4-oxazolyl, 5-oxazolyl), isoxazolyl (3-isoxazolyl, 4-isoxazolyl, 5-isoxazolyl), thiazolyl (2-thiazolyl, 4-thiazolyl, 5-thiazolyl), thiophenyl (2-thiophenyl, 3-thiophenyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2benzo[b]furanyl, 3-benzo[b]furanyl, 4-benzo[b]furanyl, 5-benzo[b]furanyl, 6-benzo[b]furanyl, 7-benzo[b]furanyl), 2,3-dihydrobenzo[b]furanyl (2-(2,3-dihydrobenzo[b]furanyl), 3-(2,3-dihydrobenzo[b]furanyl), 4-(2,3-dihydrobenzo[b]furanyl), 5-(2,3-dihydrobenzo[b]furanyl), 6-(2,3-dihydrobenzo[b]furanyl), 7-(2,3-dihydro-benzo[b]furanyl)), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydrobenzo[b]thiophenyl (2-(2,3-dihydrobenzo[b]thiophenyl), 3-(2,3-dihydro-benzo[b]thiophenyl), 4-(2,3-dihydrobenzo[b]thiophenyl), 5-(2,3-dihydrobenzo[b]-thiophenyl), 6-(2,3-dihydrobenzo[b]thiophenyl), 7-(2,3-dihydrobenzo[b]thiophenyl)), indolyl (1-indolyl, 2-indolyl, 3-indolyl, 4-indolyl, 5-indolyl, 6-indolyl, 7-indolyl), indazolyl (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepinyl (5H-dibenz[b,f]azepin-1-yl, 5H-dibenz[b,f]azepin-2-yl, 5H-dibenz[b,f]azepin-3-yl, 5H-dibenz[b,f]azepin-4-yl, 5H-dibenz[b,f]azepie-5-yl), 10,11-dihydro-5H-dibenz[b,f]azepinyl (10,11-dihydro-5H-dibenz[b,f]azepin-1-yl, 10,11-dihydro-5H-dibenz[b,f]azepin-2-yl, 10,11-dihydro-5H-dibenz[b,f]azepin-3-yl, 10,11-dihydro-5H-dibenz[b,f]azepin-4-yl, 10,11-dihydro-5H-dibenz[b,f]azepin-5-yl), piperidinyl (2-piperidinyl, 3-piperidinyl, 4-piperidinyl), pyrrolidinyl (1-pyrrolidinyl, 2-pyrrolidinyl, 3-pyrrolidinyl), phenylpyridyl (2-phenylpyridyl, 3-phenylpyridyl, 4-phenylpyridyl), phenylpyrimidinyl (2-phenylpyrimidinyl, 4-phenylpyrimidinyl, 5-phenylpyrimnidinyl, 6-phenylpyrimidinyl), phenylpyrazinyl, phenylpyridazinyl (3-phenylpyridazinyl, 4-phenylpyridazinyl, 5-phenylpyridazinyl).

The term "arylcarbonyl" (e.g. 2-thiophenylcarbonyl, 3-methoxyanthrylcarbonyl, oxazolylcarbonyl) represents an "aryl" group as defined above attached through a carbonyl group.

The term "arylalkylcarbonyl" (e.g. (2,3-dimethoxyphenyl)propylcarbonyl, (2-chloronaphthyl) pentenylcarbonyl, imidazolylcyclopentylcarbonyl) represents an "arylalkyl" group as defined above wherein the "alkyl" group is in turn attached through a carbonyl.

The compounds of the present invention have asymmetric centers and may occur as racemates, racemic mixtures, and as individual enantiomers or diastereoisomers, with all isomeric forms being included in the present invention as well as mixtures thereof.

Pharmaceutically acceptable salts of the compounds of formula 1, where a basic or acidic group is present in the structure, are also included within the scope of this invention. When an acidic substituent is present, such as —COOH or —P(O)(OH)$_2$, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, acetate, oxalate, maleate, fumarate, citrate, palmoate, methanesulfonate, p-toluenesulfonate, and the like, can be used as the dosage form.

Also, in the case of the —COOH or —P(O)(OH)$_2$ being present, pharmaceutically acceptable esters can be employed (e.g. methyl, tert-butyl, pivaloyloxymethyl, and the like), and those esters known in the art for modifying solubility or hydrolysis characteristics for use as sustained release or prodrug formulations.

In addition, some of the compounds of the instant invention may form solvates with water or common organic solvents. Such solvates are encompassed within the scope of the invention.

The term "therapeutically effective amount" shall mean that amount of drug or pharmaceutical agent that will elicit the biological or medical response of a tissue, system, animal, or human that is being sought by a researcher, veterinarian, medical doctor or other.

Preferred compounds for use according to the invention are selected from the following species:

2-{1-[N-(3-Chlorophenethyl)-N-(4-methoxybenzenesufonyl)-aminoacetyl]-4-benzyl-6-(S)-isobutyl-5-oxo-piperazin-2-yl}-N-hydroxy acetamide;

2-{1-[N-(3-Chlorophenethyl)-N-(4-methoxybenzenesufonyl)-aminoacetyl]-4-(3,5-dimethoxybenzyl)-6-(S)-isobutyl-piperazin-2-yl}-N-hydroxy acetamide;

2-{1-[N-(3-Chlorophenethyl)-N-(4-methoxybenzenesufonyl)-aminoacetyl]-4-(4-fluorobenzyl)-6-(S)-methyl-5-oxo-piperazin-2-yl}-N-hydroxy acetamide;

2-{1-[N-(3-Chlorophenethyl)-N-(4-methoxybenzenesufonyl)-aminoacetyl]-4-(4-fluorobenzyl)-5-oxo-piperazin-2-yl}-N-hydroxy-acetamide;

2-{4-(4-fluorobenzyl)-1-[N-(4-methoxybenzenesufonyl)-N-(4-methoxyphenethyl)-aminoacetyl]-5-oxo-piperazin-2-yl}-N-hydroxy-acetamide;

2-{4-(4-Fluorobenzyl)-1-[N-(4-methoxybenzenesufonyl)-N-(4-methoxyphenethyl)-aminoacetyl]-6-(S)-methyl-5-oxo-piperazin-2-yl}-N-hydroxy-acetamide;

2-{1-[N-(3-Chlorophenethyl)-N-(4-methoxybenzenesufonyl)-aminoacetyl]-4-(3,5-dimethoxybenzyl)-5-oxo-piperazin-2-yl}-N-hydroxy-acetamide;

2-{4-(3,5-Dimethoxybenzyl)-1-[N-(4-methoxybenzenesufonyl)-N-(4-methoxyphenethyl)-aminoacetyl]-5-oxo-piperazin-2-yl}-N-hydroxy-acetamide;

2-{1-[N-(3-Chlorophenethyl)-N-(4-methoxybenzenesufonyl)-aminoacetyl]4-(3,5-dimethoxybenzyl)-6-(S)-methyl-5-oxo-piperazin-2-yl}-N-hydroxy-acetamide;

2-{4-(3,5-dimethoxybenzyl)-1-[N-(4-methoxybenzenesufonyl)-N-(4-methoxyphenethyl)-aminoacetyl]-6-(S)-methyl-5-oxo-piperazin-2-yl}-N-hydroxy-acetamide;

2-{1-[N-(3-Chlorophenethyl)-N-(4-methoxybenzenesufonyl)-aminoacetyl]-4-methyl-6-(S)-methyl-5-oxo-piperazin-2-yl}-N-hydroxy-acetamide;

2-{4-Methyl-1-[N-(4-methoxybenzenesufonyl)-N-(4-methoxyphenethyl)-aminoacetyl]-6-(S)-methyl-5-oxo-piperazin-2-yl}-N-hydroxy-acetamide;

2-{4-Methyl-1-[N-(4-methoxybenzenesufonyl)-N-(3-pyridyl)-aminoacetyl]-6-(S)-methyl-5-oxo-piperazin-2-yl}-N-hydroxy-acetamide;

2-{4-Methyl-1-[N-(4-methoxybenzenesufonyl)-N-(3-ethoxypropyl)-aminoacetyl]-6-(S)-methyl-5-oxo-piperazin-2-yl}-N-hydroxy-acetamide;

2-{4-Methyl-1-[N-benzenesufonyl-N-(3-chlorophenethyl)-aminoacetyl]-6-(S)-methyl-5-oxo-piperazin-2-yl}-N-hydroxy-acetamide {1-[N-(3-Chlorophenethyl)-N-(4-methoxybenzenesufonyl)-aminoacetyl]4-(4-fluorobenzyl)-piperazin-2-yl}-N-hydroxy carboxamide;

2-{1-[N-(4-methoxyphenethyl)-N-(4-methoxybenzenesufonyl)-aminoacetyl]-6-(S)-methyl-5-oxo-piperazin-2-yl}-N-hydroxy acetamide.

Preparation of Compounds

Compounds of formula (1) may be prepared by the application or adaptation of known methods, by which is meant methods used heretofore or described in the literature. General methods for preparing compounds according to the invention may also be prepared as described in the schemes that follows.

Scheme 1 outlines general approaches to hydoxamic acids from the corresponding carboxylic acid derivatives. A carboxylate or a protected carboxylic acid of formula 1-1 can be directly converted to hydroxamic acid under an appropriate condition known in the art as described in J. Org. Chem. 54, 4091, 1989.

Alternatively, Hydrolysis of a carboxylate under standard conditions gives a free carboxylic acid which can also be coupled with hydroxylamine in the presence of suitable coupling reagent, such EDC, to give a compound of formula 1-4. If an O-protected hydroxylamine derivative known in the art, such as benzyl, t-butyldimethylsilyl or trimethylsilyl, Scheme 1

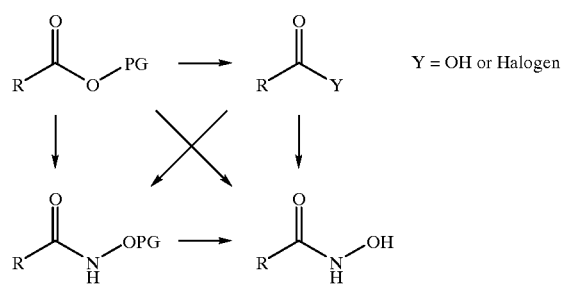

Y = OH or Halogen is used in the coupling reaction described above, a compound of formula 1-3 is obtained. Deprotection of a compound of formula 1-3 affords the corresponding hydroxamic acid compound of formula 1-4.

Scheme 2 illustrated below, refers to the preparation of compounds of the formula (I), wherein n=1, and $R_3$ is introduced from the corresponding amine used in the first step. The compound of formula 2-2 is prepared from a compound of formula 2-1, a 4-bromocrotonate derivative which can be reacted with an amine in an appropriate solvent (such as dichloromethane, DMF, THF, etc.). The subsequent coupling with an Fmoc amino acids or a Boc amino acid in the presence of DIC or EDC in a solvent, such as DMF, THF or dichloromethane, under the standard conditions gives an acylated product of formula 2-3. Removal of Fmoc protecting group can be achieved by the treatment with piperidine in DMF. A simultaneous cyclization occurs under the basic conditions to give the cyclic compounds, formula 2-4. Alternatively, Boc protecting group can be removed under the standard condition (TFA/DCM) gives a free amine derivative which then undergoes an intramolecular Michael addition in the presence of a base, such as triethylamine or DIEA.

The coupling of an α-bromo carboxylic acid under standard conditions well known in the art, results in a compound of formula 2-5 which was then treated with an amine to give an amino Scheme 2

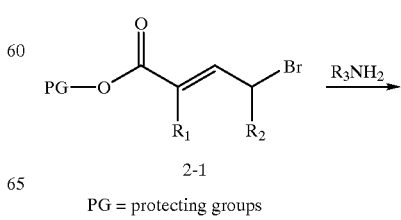

2-1

PG = protecting groups

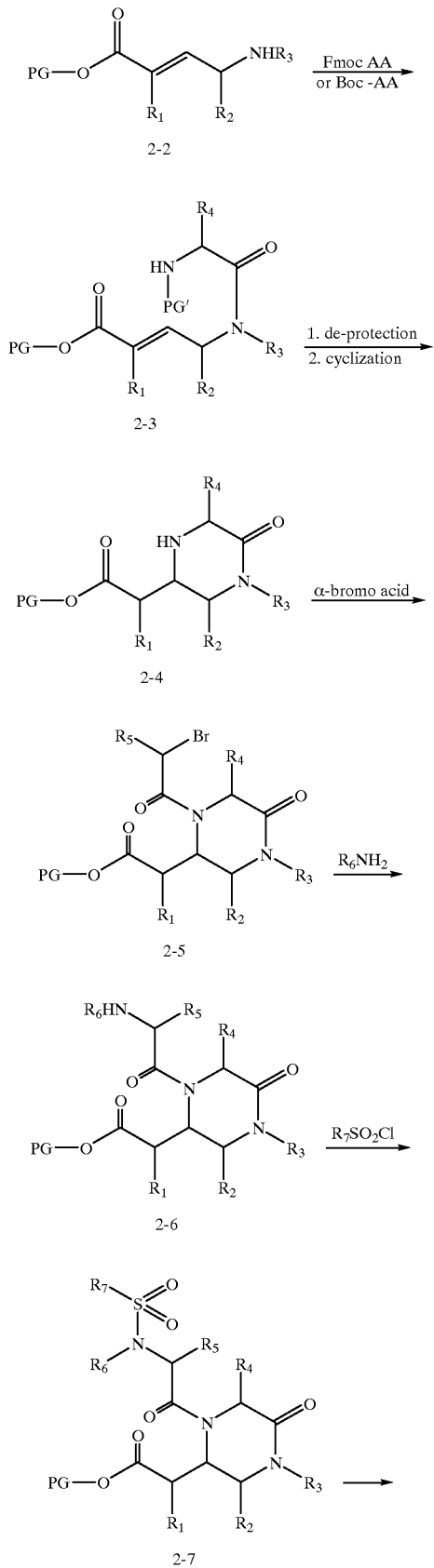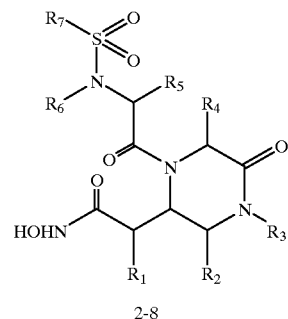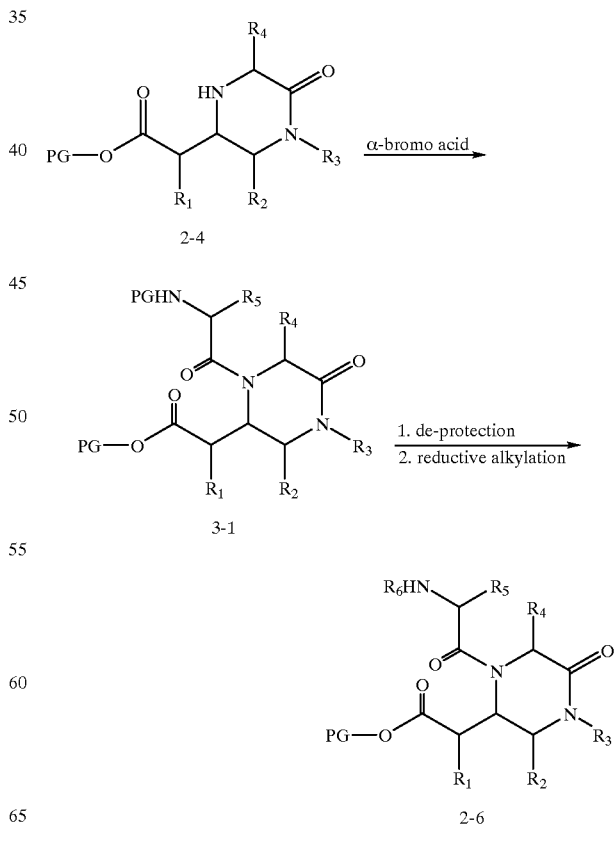

acid derivative of formula 2-6. The final compound of formula 2-8 can be readily obtained by sulfonylation followed by an appropriate step as described in Scheme 1.

Scheme 3 provides an alternative method to synthesize a compound of formula 2-6. An N-protected (Fmoc or Boc) α-amino acid can also be coupled with the compound of formula 2-4 to afford 3-1. Deprotection followed by reductive alkylation under conditions well known in the art, such as aldehyde/NaBH$_3$CN/HOAc, provide a compound of formula 2-6.

Scheme 3

Scheme 4

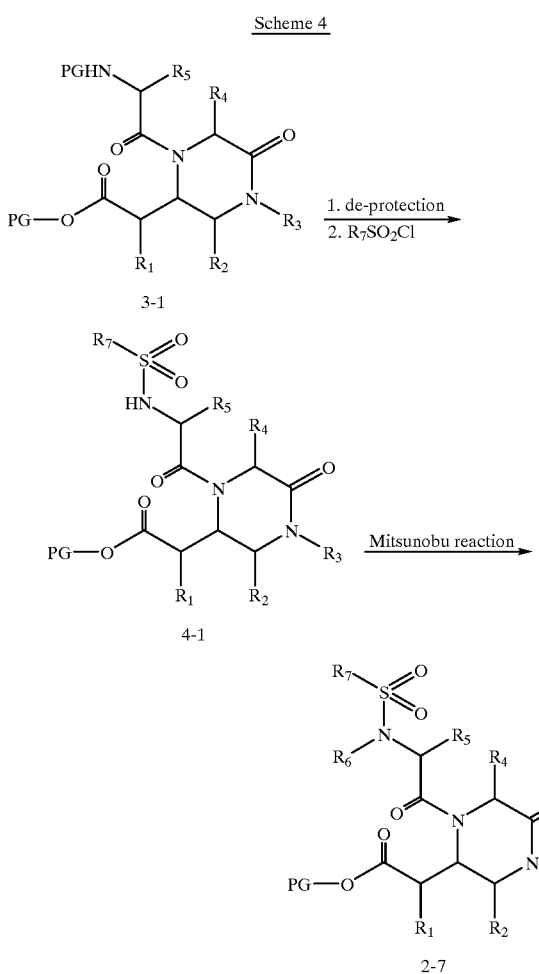

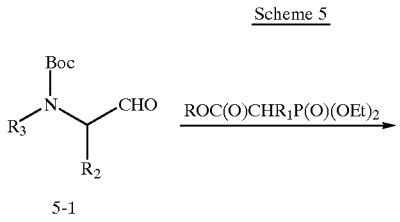

Scheme 4 illustrates an alternative method to prepare a compound of formula 2-7. Deprotection of a compound of formula 3-1 followed by sulfonylation with $R_7SO_2Cl$ gives a compound of formula 4-1. A Mitsunobu-type of reaction in the presence of $R_6OH/Ph_3P/DIAD$ affords the compound of formula 2-7.

Scheme 5 shows an alternative means for the preparation of a key intermediate of formula 2-2. Boc-α-amino aldehyde undergoes Wittig reaction by using an alkyl dialkyl

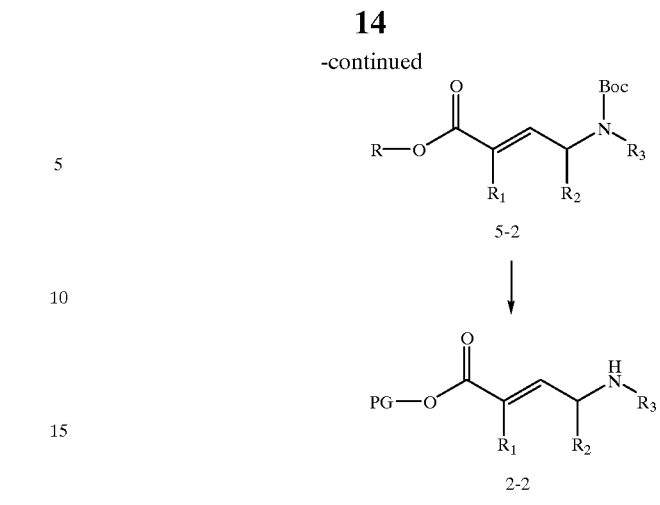

phosphonoacetate under standard conditions known in the art, as described in J. Chem. Soc., Chem. Commun. 1605 (1995) and J. Org. Chem., 56, 5729 (1991), to give an α,β-unsaturated ester. Removal Boc protecting group gives the intermediate 2-2.

Scheme 6 shows a sequence for preparation of the corresponding piperazine analogs described as formula 6-5. A reductive amination of Boc-α-amino aldehyde gives a 1,2-diamine of formula 6-2. The unprotected amino group is alkylated with a 4-bromocrotonate compound to give a precursor 6-3. An intramolecular cyclization under the same conditions as described in the Scheme 2 gives a piperazine intermediate. The same precedure can be followed for the preparation of the final compound of formula 6-5.

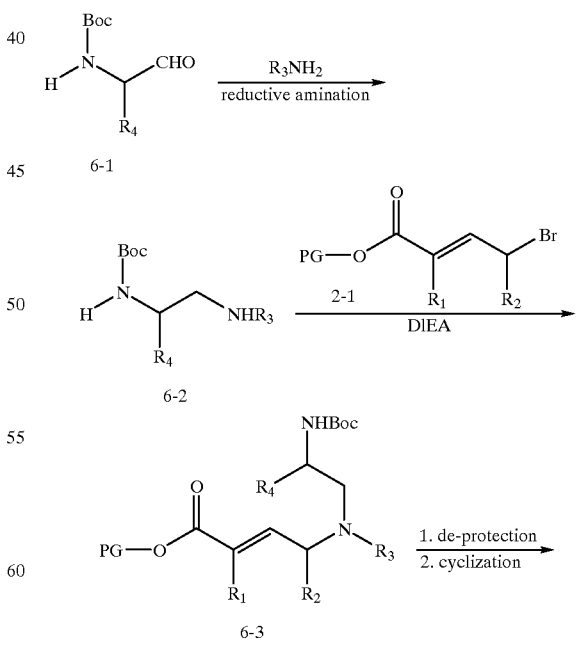

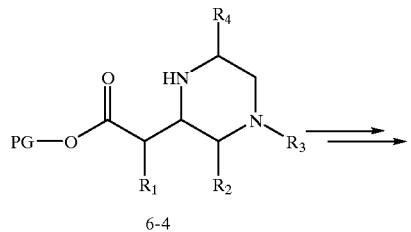

6-4

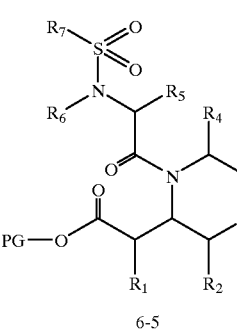

6-5

An alternative means for the preparation of these compounds according to the invention is the use of solid phase synthesis method. As shown in Scheme 7, a bromocrotonate moiety can be linked to a solid support, such as Wang resin, Merrifield resin, etc. Compared to the Scheme 2, the solid support can be considered as an alternative protecting group. However, a unique advantage of this approach is the intermediate obtained from each step is not purified, the reaction can be pushed to completion by using the excess of the reagents (usually 5–10 equiv.). A final compound is released under an appropriate cleavage condition. For example, a hydroxamic acid of formula 7-8 can be obtained directly from the resin by using an excess of hydroxylamine and base, such as triethylamine.

Scheme 7

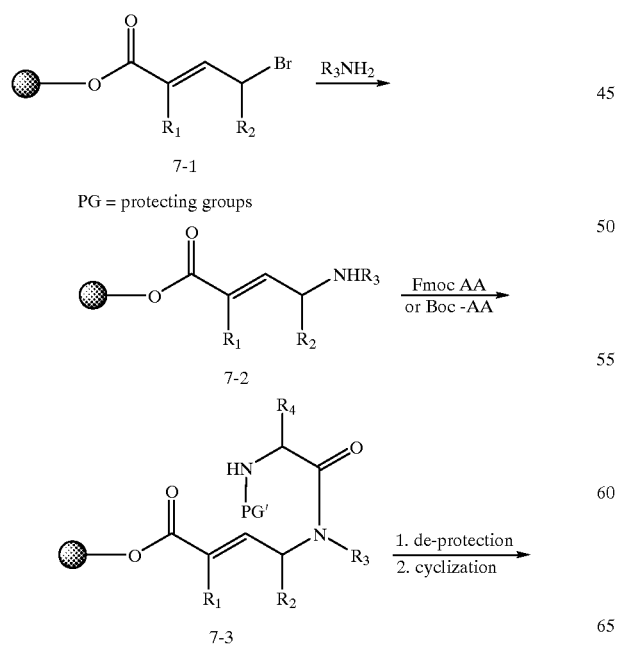

PG = protecting groups

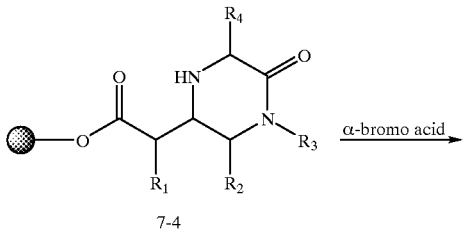

7-4

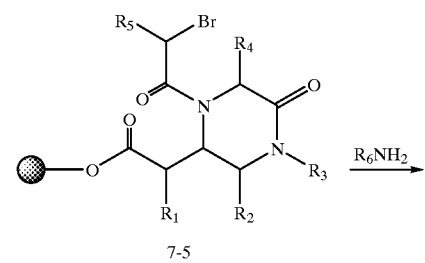

7-5

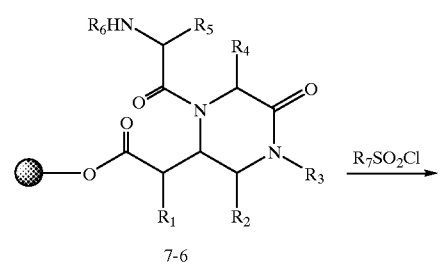

7-6

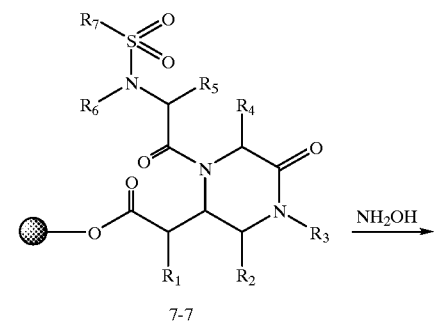

7-7

7-8

Scheme 8

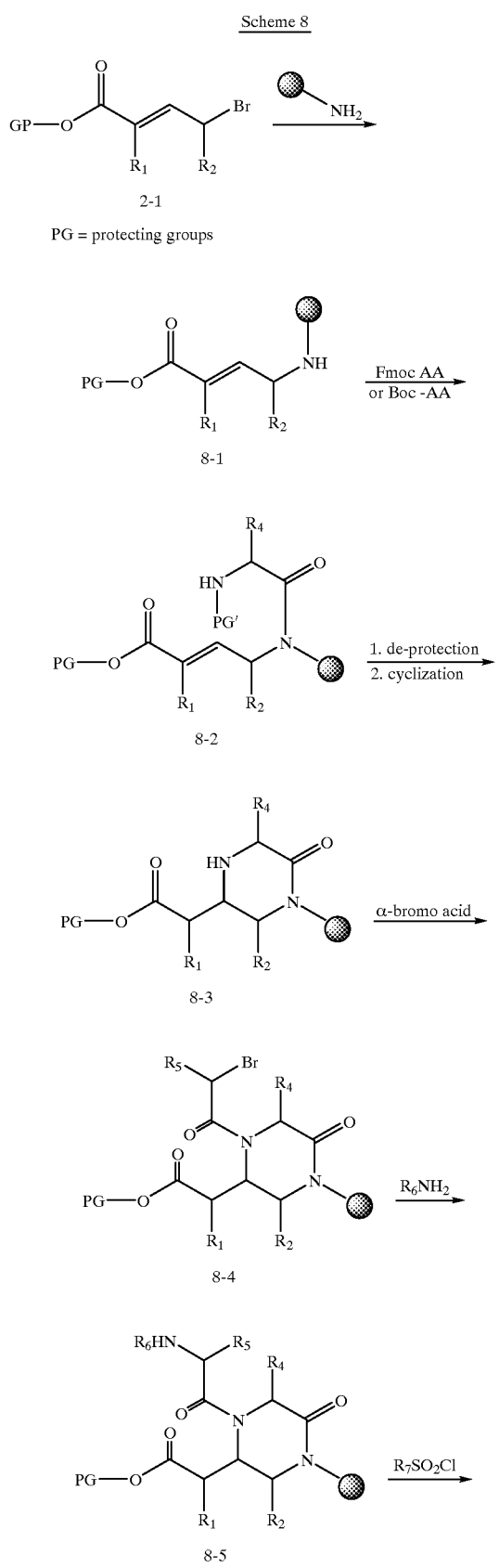

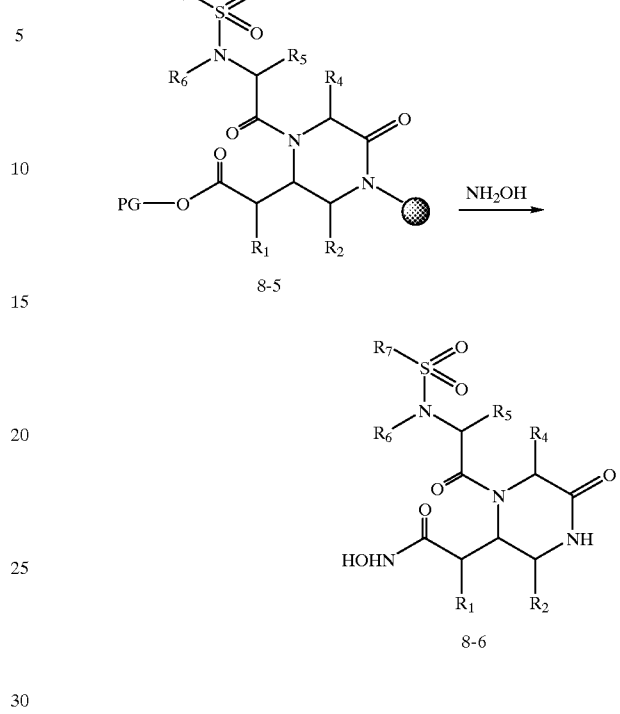

Scheme 8 illustrates a method for preparation of compounds of formula (I) where $R_3$ is hydrogen. A methyl 4-bomocrotonate template is attached to the solid support by the replacement of bromide with a free amino group. The resin used in the synthesis should be compatible to all the reaction conditions described in the scheme. However, the final product should be cleaved under mild conditions without any decomposition. According to this invention, the preferred resins include Rink resin, PAL resin and Sieber resin on which the products are cleaved under acidic conditions, such as TFA in DCM.

Under an appropriate condition, alkylation reaction can be controlled at the stage where the amino group is only mono-alkylated. The subsequent acylation with an amino acid derivative followed by de-protection and cyclization gives a piperazinone intermediate of formula 8-3. The further modification of the molecule on the solid support is achieved under similar conditions described in the Scheme 2, 3 and 4. An ester group of formula 8-5 is converted to hydroxamic acid by hydroxylamine in the presence of an appropriate base. The product of formula 8-6 is released from the solid support by using TFA in DCM.

Substituted piperazine carboxylic acids, piperazinone carboxylic acids and their derivatives, such as compounds of formula 9-1 and 9-4 described in Scheme 9 are prepared by conventional methods or according to the methods described in several patent applications, WO9720824, WO9633172 and WO9827069. Piperazine carboxylic acid, a compound of formula 9-4 where X, PG, $R_2$, $R_3$ and $R_4$ are hydrogen, is commercially available. In this case, $R_3$ can be introduced by various alkylation methods, such as N-reductive alkylation, electrophilic reaction by using alkyl halides, etc. Scheme 9 illustrates a sequence for preparation of compounds of formula (I) where n is zero. Similar to the means described above, a compound of formula 9-7 can be made by solution phase methods and solid phase technologies.

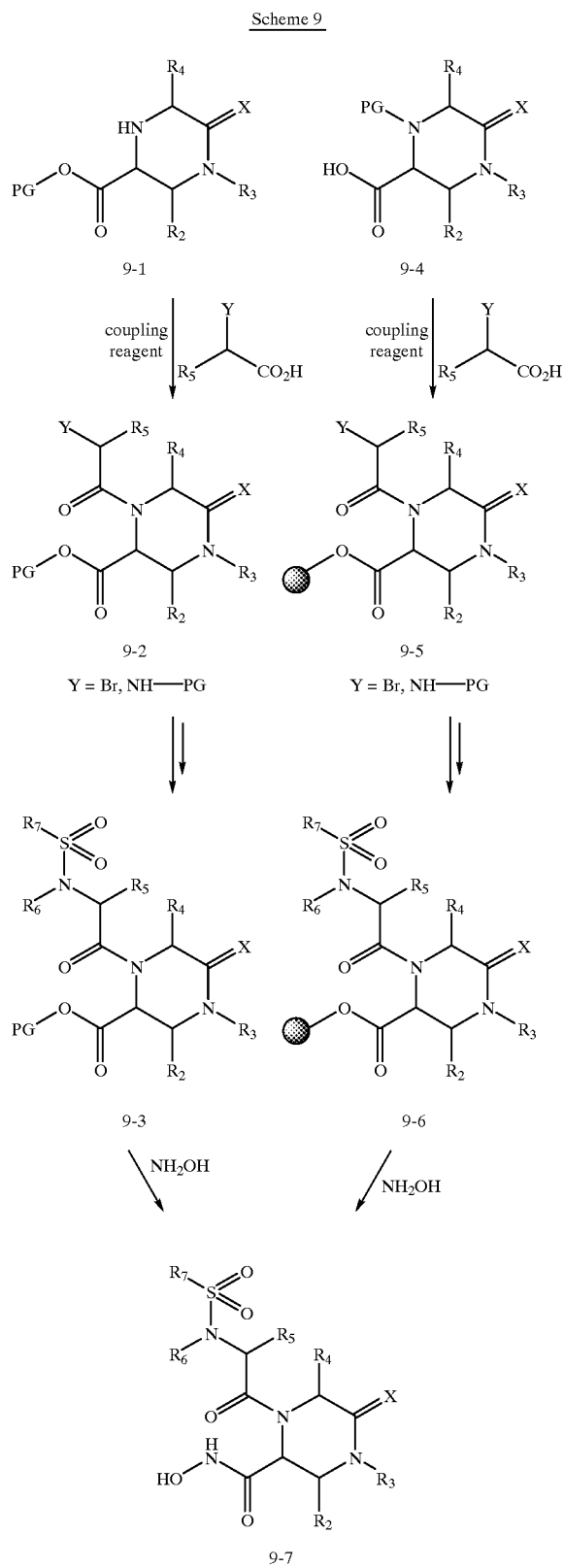

Scheme 9

EXAMPLES

The following examples are by way of illustration of various aspects of the present invention and are not intended to be limiting thereof.

General Procedures-Reagent Systems and Test Methods

Anhydrous solvents were purchased from Aldrich Chemical Company and used directly. Resins were purchased from Advanced ChemTech, Louisville, Ky., and used directly. The loading level ranged from 0.35 to 1.1 mmol/g. Unless otherwise noted, reagents were obtained from commercial suppliers and used without further purification. Preparative thin layer chromatography was preformed on silica gel pre-coated glass plates (Whatman PK5F, 150 Å, 1000 pm) and visualized with UV light, and/or ninhydrin, p-anisaldehyde, ammonium molybdate, or ferric chloride. NMR spectra were obtained on a Varian Mercury 300 MHz spectrometer. Chemical shifts are reported in ppm. Unless otherwise noted, spectra were obtained in $CDCl_3$ with residual $CHCl_3$ as an internal standard at 7.26 ppm. IR spectra were obtained on a Midac M1700 and absorbencies are listed in inverse centimeters. HPLC/MS analysis were performed on a Hewlett Packard 1100 with a photodiode array detector coupled to a Micros Platform II electrospray mass spectrometer. An evaporative light scattering detector (Sedex 55) was also incorporated for more accurate evaluation of sample purity. Reverse phase columns were purchased from YMC, Inc. (ODS-A, 3 µm, 120 Å, 4.0×50 mm).

Solvent system A consisted of 97.5% MeOH, 2.5% $H_2O$, and 0.05% TFA. Solvent system B consisted of 97.5% $H_2O$, 2.5% MeOH, and 0.05% TFA. Samples were typically acquired at a mobile phase flow rate of 2 ml/min involving a 2 minute gradient from solvent B to solvent A with 5 minute run times. Resins were washed with appropriate solvents (100 mg of resin/1 ml of solvent). Technical grade solvents were used for resin washing.

Example 1

Preparation of 2-{1-[N-(3-Chlorophenethyl)-N-(4-methoxybenzenesufonyl)-aminoacetyl]-4-benzyl-6-(S)-isobutyl-5-oxo-piperazin-2-yl}-N-hydroxy acetamide Example 1

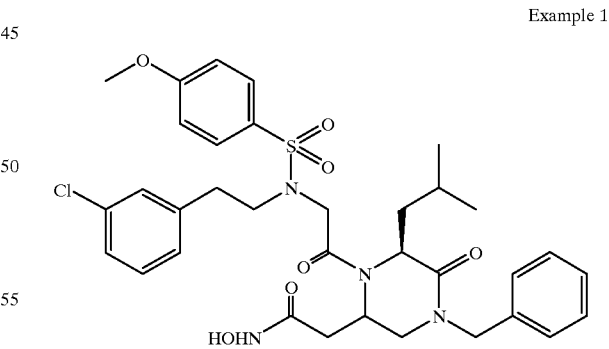

Displacement with amine: To a solution cooled at 0 C. containing methyl 4-bromocrotonate (2 mL, 17 mmol) and DCM (25 mL) were added benzyl amine (2.2 mL, 20.4 mmol) and DIEA (5.9 mL, 34 mmol). The mixture was stirred at 0 C. for 10 min, then warmed to rt with continuing stirring for 2 h at which time TLC analysis indicated the starting material had been consumed. The mixture was then concentrated and the residue was treated with EtOAc. The solid was filtered and washed with EtOAc. The combined filtrates were concentrated to give the crude product.

Acylation with an amino acid: A half amount of the crude product obtained from the previous step was added to a mixture of Fmoc-L-Leu-OH (3.5 g, 10 mmol) and DCM (20 mL). After the resulting mixture was cooled to 0 C., EDC (1.9 g, 10 mmol) was added. The mixture was stirred for 15 min, then warmed to room temperature with stirring for another 3 h. The mixture was diluted with EtOAc, washed with 1N HCl, water and brine. The organic layer was dried over $Na_2SO_4$. Filtration followed by concentration gave a residue which was purified by flash chromatography on silica gel (2.6 g, 56%). MS (ES) m/e: 541 (M+H⁺).

Deprotection and cyclization: The above Fmoc-Leu coupled product (1.08 g, 2 mmol) was treated with 5% piperidine in DCM for 30 min. The solution was concentrated, and the residue was diluted with EtOAc, and then washed with $H_2O$. The organic layer was dried over $Na_2SO_4$. Filtration and concentration gave the crude cyclic product which was dried in vacuo, then dissolved in DCM (10 mL).

Bromoacetylation: To this was added bromoacetic acid (556 mg, 4 mmol) followed by addition of EDC (767 mg, 4 mmol). After stirring at rt for 3 h, the mixture was poured into ice-water, extracted with EtOAc. The organic layer was washed with a dilute citric acid solution, then with water. The obtained crude product was dried in vacuo overnight.

Displacement with amine and sulfonylation: The above obtained crude product was dissolved in DCM (20 mL). To the solution cooled to 0 C. was added 3-chlorophenethyl amine (373 mg, 2.4 mmol) and DIEA (516 mg, 4 mmol). The mixture was stirred at 0 C. for 2 h at which time TLC indicated the reaction was completed. 4-Methoxybenzenesulfonyl chloride (620 mg, 3 mmol) was added. The resulting mixture was stirred for additional 30 min, then at rt for 2 h. The mixture was poured into ice-water, extracted with EtOAc. The organic layer was then washed successively with sat. $NaHCO_3$ and brine. The crude product was purified by flash chromatography on silica gel column to give pure compound (0.71 g, 52%).

MS (ES) m/e: 684 (M+H⁺).

Hydroxamic acid: To a stirred solution of hydroxylamine hydrochloride (1.6 g, 23 mmol) in methanol (15 mL) was added a solution of KOH (2.0 g, 17 mmol) in methanol (10 mL) at room temperature. Removal of the precipitated salt by filtration gave a solution of hydroxylamine in methanol. The methyl ester prepared above (10 mg, 14.6 μmol) was added to the hydroxylamine solution (0.3 mL) and the mixture was stirred overnight at rt. The reaction mixture was poured into 5% HCl and extracted with EtOAc, and the organic layer was washed with water and dried ($Na_2SO_4$). Evaporation of the solvent afforded the desired product as colorless syrup (4 mg, 40 %). MS (ES) m/e: 685 (M+H⁺).

Example 2

Preparation of 2-{1-[N-(3-Chlorophenethyl)-N-(4-methoxybenzenesufonyl)-aminoacetyl]-4-(3,5-dimethoxybenzyl)-6-(S)-isobutyl-piperazin-2-yl}-N-hydroxy acetamide Example 2

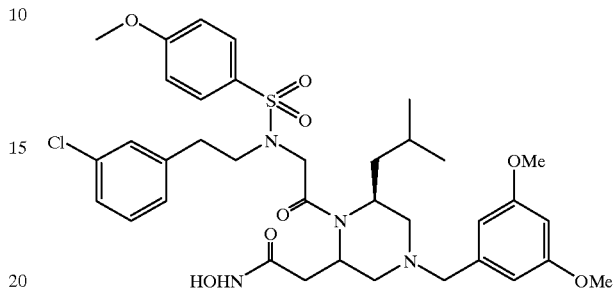

Reductive amination: To a mixture of Boc-L-Leu-CHO (1.17 g, 5.5 mmol) in DCM (30 ML) were added trimethyl orthoformate (1.18 mL, 10.8 mmol), 3,5-dimethoxybenzylamine (1 g, 5.9 mmol) and a catalytic amount of HOAc (0.2 mL). The resulting mixture was stirred at rt for 4 h. The mixture was concentrated and dried in vacuo. The obtained imine was dissolved in 10 mL of MeOH. To this solution was added sodium cyanoborohydride (650 mg, 11 mmol). The resulting mixture was stirred at rt overnight, then poured into ice water with stirring for 5 min, extracted with EtOAc. The organic layer was washed with sat. $NaHCO_3$ and brine. Concentration gave the crude product which was purified by flash chromatography on silica gel (1.4 g, 70% yield).

N-alkylation with methyl 4-bromocrotonate: To a solution of the amine prepared above (366 mg, 1 mmol) and DIEA (258 mg, 2 mmol) in DCM (5 mL) cooled at 0 C. was added methyl 4-bromocrotonate (215 mg, 1.2 mmol). The mixture was stirred at 0 C. for 10 min, then warmed to rt. Stirring continued for 12 h at which time TLC analysis indicated the starting material had been consumed. The mixture was then concentrated and the residue was treated with EtOAc. The solid was filtered and washed with EtOAc. The combined filtrates were concentrated to give the crude product which was purified by flash chromatography on silica gel (250 mg, 54% yield).

MS (ES) m/e: 465 (M+H⁺).

De-protection and cyclization: The obtained product from the previous step (100 mg) was treated with 20% TFA in DCM (0.5 mL) at rt for 15 min. The mixture was then evaporated to give a residue which was dissolved in DCM (5 mL). The solution was then washed with sat. $NaHCO_3$. DIEA (5 mmol) was added. After stirring for 30 min, the mixture was concentrated to give the crude cyclic product which was directly used for the next step without further purification. MS (ES) m/e: 365 (M+H⁺).

A similar procedure was followed as described in the Example 1 to complete the synthetic sequence, which includes bromoacetylation, amine displacement, sulfonylation and hydroxylamine exchange reaction. MS (ES) m/e: 731 (M+H⁺).

Example 3

Preparation of 2-{1-[N-(3-Chlorophenethyl)-N-(4-methoxybenzenesufonyl)-aminoacetyl]-4-(4-fluorobenzyl)-6-(S)-methyl-5-oxo-piperazin-2-yl}-N-hydroxy acetamide Example 3

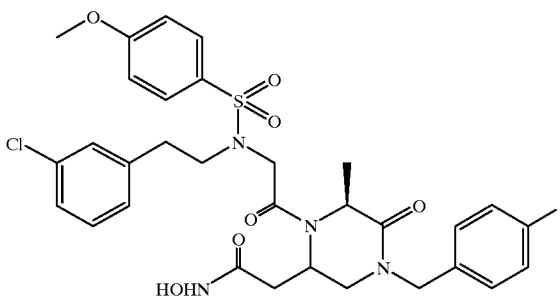

Displacement of bromide: 4-Bromocrotonate Merrifield Resin (450 mg, loading 0.6 mmol/g) was suspended in a solution of 4-fluorobenzyl amine [0.5M]in NMP (8 mL) and the resulting suspension was shaken for 45 min at room temperature. After filtration, the resin was washed with 2×10 mL of DMF, 3×10 mL of DCM/MeOH, 2×10 mL of DCM then dried under nitrogen. IR(KBr): 1720 cm$^{-1}$.

Acylation: To the resin were added Fmoc-L-alanine (10 eq), DIC (10 eq), and DMF (3 mL/100 mg of resin). The resulting mixture was shaken for 24 h at room temperature. After filtration, the resin was washed with 2×DMF (3 mL/100 mg of resin), 2×DCM/MeOH, 2×DCM then dried under nitrogen.

Deprotection and cyclization: The resin was suspended in a solution of piperidine (20%) in DMF (3 mL/100 mg of resin) and shaken for 30 min. After filtration, the resin was washed with 2×DMF (3 mL/100 mg of resin), 2×DCM/MeOH, 2×DCM then dried under nitrogen. IR (KBr): 1734 cm$^{-1}$.

Bromoacetylation, amine displacement and sulfonylation: To the resin were added 1 M solutions of bromoacetic acid in DMF (3 mL) and DIC in DMF (3 mL). The resulting suspension was shaken at rt for 3 h. Filtration followed by successively washing with DMF (2×), MeOH/DCM (3×) and DCM (3×). The obtained resin was treated with a 0.5 M solution of 3-chlorophenethyl amine in NMP (0.5 mL). After mixing for 6 h, the resin was filtered and washed with DMF (2×), MeOH/DCM (3×) and DCM (3×), and dried under reduced pressure. The resin was then mixed with a 0.1 M solution of DMAP in 3:2 pyridine/DCM (3 mL) and a 0.5 M solution of 4-methoxybenzene-sufonyl chloride (3 mL). The suspension was shaken for 12 h. Filtration followed by washing with DMF (3×), MeOH/DCM (3×) and DCM (3×) gave the resin which was dried under reduced pressure.

Preparation of hydroxylamine solution and cleavage: Potassium t-butoxide (25.35 g, 0.207 mol) was added slowly to methanol (50 mL) pre-cooled at 0 C. After completion of the addition, stirring continued until the solid was completely dissolved. The solution was then added dropwise to a mixture of hydroxylamine hydrochloride (13.9 g, 0.20 mol) and methanol (50 mL) cooled in an ice-bath. After completion of the addition, the suspension was stirred for another 5 min, then filtered. The filtrate (2M solution of hydroxylamine in methanol) was then mixed with a 2:1 mixture of Et3N/THF (100 mL) to give a solution for use of cleavage. The resin obtained from the previous step (100 mg) was treated with 2 mL of the freshly prepared solution of NH$_2$OH/Et$_3$N in MeOH/THF. The suspension was shaken for 30 min at rt. The resin was filtered and washed with THF. The combined filtrates were concentrated to give the hydroxamic acid compound which was purified on a preparative TLC plate. MS (ES) m/e: 661 (M+H$^+$).

Examples 4–15

The following compounds are made using the method described above.

| EXAMPLES | R$_3$ | R$_4$ | R$_6$ | R$_7$ |
|---|---|---|---|---|
| 4 | 4-fluorobenzyl | H | 3-chlorophenethyl | 4-methoxyphenyl |
| 5 | 4-fluorobenzyl | H | 4-methoxy-phenethyl | 4-methoxyphenyl |
| 6 | 4-fluorobenzyl | Me | 4-methoxy-phenethyl | 4-methoxyphenyl |
| 7 | 3,5-dimethoxy-benzyl | H | 3-chlorophenethyl | 4-methoxyphenyl |
| 8 | 3,5-dimethoxy-benzyl | H | 4-methoxy-phenethyl | 4-methoxyphenyl |
| 9 | 3,5-dimethoxy-benzyl | Me | 3-chlorophenethyl | 4-methoxyphenyl |
| 10 | 3,5-dimethoxy-benzyl | Me | 4-methoxy-phenethyl | 4-methoxyphenyl |
| 11 | Me | Me | 3-chlorophenethyl | 4-methoxyphenyl |
| 12 | Me | Me | 4-methoxy-phenethyl | 4-methoxyphenyl |
| 13 | Me | Me | 3-pyridylmethyl | 4-methoxyphenyl |
| 14 | Me | Me | 3-ethoxypropyl | 4-methoxyphenyl |
| 15 | Me | Me | 3-chlorophenethyl | phenyl |

Example 16

Preparation of {1-[N-(3-Chlorophenethyl)-N-(4-methoxybenzenesufonyl)-aminoacetyl]-4-(4-fluorobenzyl)-piperazin-2-yl}-N-hydroxy carboxanide Example 4

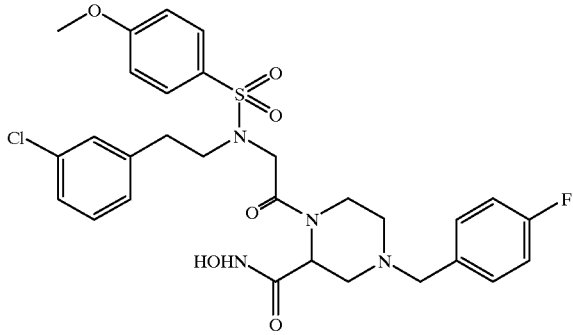

N-alkylation: N$^1$-Boc-N$^4$-Fmoc-2-piperazinecarboxylate Merrifield (0.5 g, 0.6 mmol/g) was treated with 20% piperidine in DMF at room temperature for 30 min. The mixture was filtered and the resin was washed with DMF (3×), MeOH/DCM (5×) and DCM (3×). After drying under reduced pressure, the resin was mixed with 4-fluorobenzyl bromide (mL, 10 equiv.), and DMF (3.5 mL). The resulting slurry was shaken at room temperature for 12 h. The resin was filtered, and washed with DMF (2×), MeOH/DCM (3×), and DMF (3×). The obtained resin was dried under reduced pressure.

Acylation: The above resin was treated with 20% TFA in DCM (5 mL) for 30 min, then washed with DCM (6×) and 1 M DIEA in DCM (5 mL). The dried resin was treated 1 M solutions of bromoacetic acid in DMF (3 mL) and DIC in DMF (3 mL). The suspension was shaken for 3 h at room temperature. The resin was filtered, washed with DMF (3×), MeOH/DCM (5×) and DCM (3×).

A similar procedure was followed as described in the Example 3 to complete the synthetic sequence, which includes amine displacement, sulfonylation and cleavage with hydroxylamine.

MS (ES) m/e: 619.5 (M+H$^+$).

Example 17

Preparation of 2-{1-[N-(4-methoxyphenethyl)-N-(4-methoxybenzenesufonyl)-aminoacetyl]-6(S)-methyl-5-oxo-piperazin-2-yl}-N-hydroxy acetamide Example 17

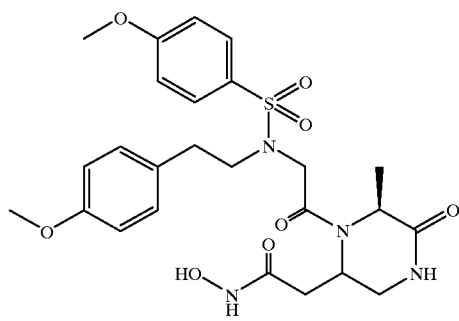

Alkylation: Rink resin (3.5 g, 0.7 mmol/g) was added to a mixture of THF (10 mL), 1 M methyl 4-bromocrotonate in THF (14.7 mL) and 1 M DIEA in THF (3.7 mL). The suspension was shaken at rt for 6 h. The resin was then filtered, and washed with DMF (3×), MeOH/DCM (3×), DCM (3×), dried under reduced pressure.

Acylation and cyclization: The above obtained resin (1 g) was mixed with 1M DIC in DMF (7 mL) and 1 M Fmoc-Ala-OH in DMF (7 mL). After shaking for 24 h at rt, filtration followed by washing (DMF, MeOH/DCM and DCM, 3×) gave the resin which was then treated with 20% piperidine in DMF. After stirring for 30 min at rt, the resin was filtered and washed as usual. The resin was dried under reduced pressure.

Bromoacetylation and amine displacement: The resin was mixed with 1 M solution of bromoacetic acid in DMF (4.2 mL) and 1 M DIC in DMF (4.2 mL), and stirred at rt for 3 h. After filtration, the resin was washed and dried as usual. The above process was repeated, and the resin was then suspended in a 1M solution of 4-methoxyphenethyl amine in DMF (7 mL). After stirring for 12 h, filtration followed by washing afforded resin which was then subjected to sulfonylation.

Sulfonylation: The above resin was added to a mixture of 0.1 M DMAP in pyridine (6 mL) and DCE (4 mL). 4-Methoxybenzenesulfonyl chloride (1.45 g, 7 mmol) was added. The resulting suspension was stirred at rt for 12 h. Filtration followed by washing provided the resin which was dried under reduced pressure.

Hydroxamic acid formation and cleavage: The above resin (100 mg) was treated with 2 mL of a freshly prepared hydroxylamine solution (to see example 3) for 3 h at rt. The resin was filtered and washed with MeOH, DMF and DCM at least 3 times respectively, then mixed with 2 mL of 20% TFA in DCM for 30 min. The resin was filtered and washed with 2 mL of DCM. The combined filtrates were concentrated to give crude hydroxamic acid product which was confirmed by LC-MS analysis [MS (ES): m/e 549.3 (M+H$^+$)]. The pure compound was obtained by purification on a preparative TLC plate.

Biological Results

Each of the compounds of Examples 5–12 were assayed for their efficacy as MMP-9 inhibitors. The assay for MMP-9 inhibitors was performed by mixing purified MMP-9 enzyme with assay buffer, substrate, and compound to be tested. The substrate is an internally quenched fluorescent peptide that becomes unquenched upon cleavage by MMP-9 enzyme. After incubation at 37 C., the assay is stopped by addition of EDTA solution and the fluorescence is measured. The fluorescence is directly proportional to enzyme activity. A compound that is an inhibitor of MMP-9 activity will reduce the resultant fluorescent values. The assay results are set forth in Table 1 below.

TABLE 1

| Examples | IC50($\mu$M) | % inhibition @ 1 $\mu$M |
|---|---|---|
| 3A (isomer A) | 0.05 | |
| 3B (isomer B) | 0.053 | |
| 4 | | 52% |
| 5 | | 42% |
| 6 | 0.10 | |
| 7 | | 62% |
| 8 | | 35% |
| 9 | 0.12 | |
| 10 | 0.15 | |

Having defined the invention we claim:

1. A compound having the structure and pharmaceutical acceptable salts thereof;

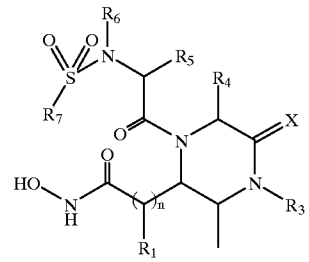

wherein:
the broken line represents an optional double bond;
X is H or O;
n is 0 or 1;
$R_1$ is hydrogen, trifluoromethyl, $C_1$–$C_6$ alkyl, $C_2$–$C_6$ alkenyl, said alkyl and alkenyl optionally substituted with 1 to 3 groups of $R_s$;

R$_2$ is hydrogen, trifluoromethyl, C$_1$–C$_6$ alkyl, C$_1$–C$_6$ alkenyl, said alkyl, alkenyl optionally substituted with 1 to 3 groups of R$_s$;

R$_3$ and R$_4$ independently are hydrogen, trifluoromethyl, C$_5$–C$_{10}$ aryl, C$_5$–C$_{10}$ heteroaryl, C$_1$–C$_{10}$ alkyl, C$_2$–C$_{10}$ alkenyl, C$_2$–C$_{10}$ alkynyl, C$_3$–C$_{10}$ cycloalkyl, C$_4$–C$_{10}$ heterocyclyl, C$_5$–C$_{10}$ aryl-C$_1$–C$_{10}$ alkyl, C$_5$–C$_{10}$ heteroaryl-C$_1$–C$_{10}$ alkyl, —COR$_8$, —CO$_2$R$_8$, —CONR$_8$R$_9$, —SO$_2$NR$_8$R$_9$, said aryl, heteroaryl, alkyl, alkenyl, cycloalkyl, and heterocyclyl optionally substituted with 1 to 3 groups of R$_s$;

R$_5$ is hydrogen, trifluoromethyl, C$_1$–C$_6$ alkyl, C$_1$–C$_6$ alkenyl, said alkyl and alkenyl optionally substituted with 1 to 3 groups of R$_s$;

R$_6$ is hydrogen, trifluoromethyl, C$_5$–C$_{10}$ aryl, C$_5$–C$_{10}$ heteroaryl, C$_1$–C$_{10}$ alkyl, C$_2$–C$_{10}$ alkenyl, C$_2$–C$_{10}$ alkynyl, C$_3$–C$_{10}$ cycloalkyl, C$_4$–C$_{10}$ heterocyclyl, C$_5$–C$_{10}$ aryl-C$_1$–C$_{10}$ alkyl, C$_5$–C$_{10}$ heteroaryl-C$_1$–C$_{10}$ alkyl, said aryl, heteroaryl, alkyl, alkenyl, cycloalkyl, and heterocyclyl optionally substituted with 1 to 3 groups of R$_s$;

R$_7$ is C$_5$–C$_{10}$ aryl, C$_5$–C$_{10}$ heteroaryl, C$_1$–C$_6$ alkyl, C$_2$–C$_6$ alkenyl, C$_3$–C$_6$ cycloalkyl, C$_4$–C$_{10}$ heterocyclyl, said aryl, heteroaryl, alkyl, alkenyl, and cycloalkyl optionally substituted with 1 to 3 groups of R$_s$;

R$_8$ and R$_9$ independently are hydrogen, hydroxy, C$_1$–C$_6$ alkyl, C$_2$–C$_6$ alkenyl, C$_2$–C$_6$ alkynyl, C$_3$–C$_7$ cycloalkyl, C$_4$–C$_{10}$ heterocyclyl, C$_5$–C$_{10}$ aryl, C$_5$–C$_{10}$ heteroaryl;

R$_s$ represents a member selected from the group consisting of halo, cyano, nitro, trihalomethyl, carbamoyl, hydroxy, trifluoromethoxy acyl, aryl, heteroaryl, —S(O)R$_8$, =N(OR$_8$), —SO$_2$R$_8$, —COOR$_8$, —CONR$_8$R$_9$, —C$_1$–C$_6$alkylCONR$_8$R$_9$, C$_1$–C$_6$alkyloxy, aryloxy, arylC$_1$–C$_6$alkyloxy, thio, C$_1$–C$_6$alkylthio, arylthio, arylC$_1$–C$_6$alkylthio, NR$_7$R$_8$, C$_1$–C$_6$alkylamino, arylamino, arylC$_1$–C$_6$alkylamino, di(arylC$_1$–C$_6$alkyl)amino, C$_1$–C$_6$alkylcarbonyl, arylC$_1$–C$_6$alkylcarbonyl, C$_1$–C$_6$alkylcarboxy, arylC$_1$–C$_6$alkylcarboxy, —NR$_9$CO$_2$R$_8$, —NR$_9$COR$_8$, —NR$_9$O$_2$R$_8$, —NR$_9$O$_2$R$_8$, —CONR$_8$R$_9$, —SO$_2$NR$_8$R$_9$, —OCONR$_8$R$_9$, —C$_1$–C$_6$alkylaminoCONR$_8$R$_9$, arylC$_1$–C$_6$alkylcarbonylamino, tetrahydrofuryl, morpholinyl, piperazinyl, or a saturated or partial saturated cyclic 5,6 or 7 membered amine or lactam.

2. A compound according to claim 1, wherein X is oxygen.

3. A compound according to claim 1, wherein R$_1$, R$_2$ and R$_5$ are hydrogen.

4. A compound according to claim 1, wherein R$_3$ is optionally substituted C$_1$–C$_{10}$alkyl and C$_5$–C$_{10}$aryl-C$_1$–C$_{10}$ alkyl.

5. A compound according to claim 1, wherein R$_4$ is hydrogen or methyl.

6. A compound according to claim 1, wherein R$_7$ is optionally substituted aryl.

7. A compound according to claim 6, wherein aryl is 4-methoxyphenyl.

8. A compound according to claim 1, which is selected from the group consisting of:

2-{1-[N-(3-Chlorophenethyl)-N-(4-methoxybenzenesufonyl)-aminoacetyl]-4-benzyl-6-(S)-isobutyl-5-oxo-piperazin-2-yl}-N-hydroxy acetamide;

2-{1-[N-(3-Chlorophenethyl)-N-(4-methoxybenzenesufonyl)-aminoacetyl]-4-(3,5-dimethoxybenzyl)-6-(S)-isobutyl-piperazin-2-yl}-N-hydroxy acetamide;

2-{1-[N-(3-Chlorophenethyl)-N-(4-methoxybenzenesufonyl)-aminoacetyl]-4-(4-fluorobenzyl)-6-(S)-methyl-5-oxo-piperazin-2-yl}-N-hydroxy acetamide;

2-{1-[N-(3-Chlorophenethyl)-N-(4-methoxybenzenesufonyl)-aminoacetyl]-4-(4-fluorobenzyl)-5-oxo-piperazin-2-yl}-N-hydroxy-acetamide;

2-{4-(4-fluorobenzyl)-1-[N-(4-methoxybenzenesufonyl)-N-(4-methoxyphenethyl)-aminoacetyl]-5-oxo-piperazin-2-yl}-N-hydroxy-acetamide;

2-{4-(4-Fluorobenzyl)-1-[N-(4-methoxybenzenesufonyl)-N-(4-methoxyphenethyl)-aminoacetyl]-6-(S)-methyl-5-oxo-piperazin-2-yl}-N-hydroxy-acetamide;

2-{1-[N-(3-Chlorophenethyl)-N-(4-methoxybenzenesufonyl)-aminoacetyl]-4-(3,5-dimethoxybenzyl)-5-oxo-piperazin-2-yl}-N-hydroxy-acetamide;

2-{4-(3,5-Dimethoxybenzyl)-1-[N-(4-methoxybenzenesufonyl)-N-(4-methoxyphenethyl)-aminoacetyl]-5-oxo-piperazin-2-yl}-N-hydroxy-acetamide;

2-{1-[N-(3-Chlorophenethyl)-N-(4-methoxybenzenesufonyl)-aminoacetyl]-4-(3,5-dimethoxybenzyl)-6-(S)-methyl-5-oxo-piperazin-2-yl}-N-hydroxy-acetamide;

2-{4-(3,5-dimethoxybenzyl)-1-[N-(4-methoxybenzenesufonyl)-N-(4-methoxyphenethyl)-aminoacetyl]-6-(S)-methyl-5-oxo-piperazin-2-yl}-N-hydroxy-acetamide 2-{1-[N-(3-Chlorophenethyl)-N-(4-methoxybenzenesufonyl)-aminoacetyl]4-methyl-6-(S)-methyl-5-oxo-piperazin-2-yl}-N-hydroxy-acetamide;

2-{4-Methyl-1-[N-(4-methoxybenzenesufonyl)-N-(4-methoxyphenethyl)-aminoacetyl]-6-(S)-methyl-5-oxo-piperazin-2-yl}-N-hydroxy-acetamide;

2-{4-Methyl-1-[N-(4-methoxybenzenesufonyl)-N-(3-pyridyl)-aminoacetyl]-6-(S)-methyl-5-oxo-piperazin-2-yl}-N-hydroxy-acetamide;

2-{4-Methyl-1-[N-(4-methoxybenzenesufonyl)-N-(3-ethoxypropyl)-aminoacetyl]-6-(S)-methyl-5-oxo-piperazin-2-yl}-N-hydroxy-acetamide;

2-{4-Methyl-1-[N-benzenesufonyl-N-(3-chlorophenethyl)-aminoacetyl]-6-(S)-methyl-5-oxo-piperazin-2-yl}-N-hydroxy-acetamide {1-[N-(3-Chlorophenethyl)-N-(4-methoxybenzenesufonyl)-aminoacetyl]-4-(4-fluorobenzyl)-piperazin-2-yl}-N-hydroxy carboxamide;

2-{1-[N-(4-methoxyphenethyl)-N-(4-methoxybenzenesufonyl)-aminoacetyl]-6-(S)-methyl-5-oxo-piperazin-2-yl}-N-hydroxy acetamide.

9. A pharmaceutical composition which comprises a compound according to claim 1 or the pharmaceutically acceptable salts thereof and a pharmaceutically acceptable carrier.

10. The pharmaceutical composition of claim 9 prepared by admixing said compound with a material selected from the group consisting of a pharmaceutically acceptable salt thereof, a pharmaceutically acceptable carrier, a pharmaceutically acceptable excipient and combinations thereof.

* * * * *